United States Patent [19]

Okuchi et al.

[11] Patent Number: 4,468,350
[45] Date of Patent: Aug. 28, 1984

[54] KA-6643-SERIES ANTIBIOTICS, PROCESS FOR PRODUCING SAME AND MEDICAL COMPOSITION CONTAINING SAME

[75] Inventors: Masao Okuchi, Tokorozawa; Masahito Nakayama, Higashi-Yamato; Akio Iwasaki, Kawasaki; Shigeru Kimura, Tachikawa; Toshimi Mizoguchi, Higashi-Murayama; Sohei Tanabe, Higashi-Murayama; Akira Murakami, Higashi-Murayama; Hisakatsu Ito, Kawagoe; Toshihito Mori, Higashi-Murayama, all of Japan

[73] Assignee: Kowa Co., Ltd., Nagoya, Japan

[21] Appl. No.: 314,028

[22] Filed: Oct. 22, 1981

[30] Foreign Application Priority Data

Oct. 24, 1980 [JP] Japan ................. 55-149177
Mar. 6, 1981 [JP] Japan ................. 56-31983
Jul. 27, 1981 [JP] Japan ................. 56-117449

[51] Int. Cl.³ .......................... C07D 487/04
[52] U.S. Cl. ................... 260/245.2 T; 424/274; 435/119
[58] Field of Search ............... 260/245.2 T; 424/274

[56] References Cited

U.S. PATENT DOCUMENTS

| 4,146,610 | 3/1979 | Cole et al. | 260/245.2 T |
| 4,162,304 | 7/1979 | Box et al. | 260/245.2 T |
| 4,162,324 | 7/1979 | Cassidy et al. | 260/245.2 T |
| 4,223,038 | 9/1980 | Smale | 260/245.2 T |
| 4,409,147 | 10/1983 | Asai et al. | 260/245.2 T |

FOREIGN PATENT DOCUMENTS

| 8497 | 3/1980 | European Pat. Off. | 260/245.2 T |
| 0008497 | 3/1980 | European Pat. Off. . | |
| 0030719 | 6/1981 | European Pat. Off. . | |
| 2071099A | 9/1981 | European Pat. Off. . | |
| 2042532A | 9/1980 | United Kingdom . | |

Primary Examiner—Mary C. Lee
Attorney, Agent, or Firm—Oblon, Fisher, Spivak, McClelland & Maier

[57] ABSTRACT

A-KA-6643-series antibiotic comprising at least one substance represented by any of the following formulae, or a salt or ester thereof:

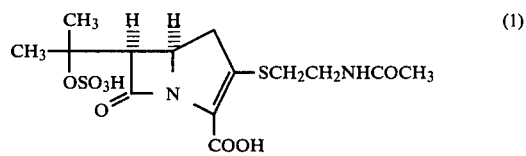

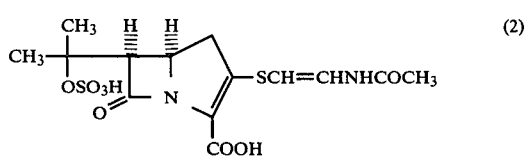

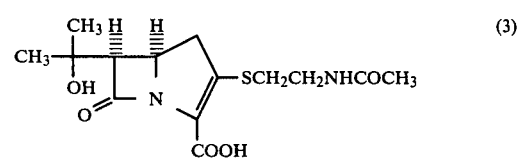

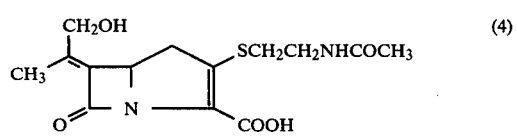

is effectively useful as an antibacterial and $\beta$-lactamase inhibiting agent.

4 Claims, 9 Drawing Figures

KA-6643-SERIES ANTIBIOTICS, PROCESS FOR PRODUCING SAME AND MEDICAL COMPOSITION CONTAINING SAME

BACKGROUND OF THE INVENTION

1. Field of the Invention

This invention relates to novel KA-6643-series antibiotics and salts and esters thereof, their preparation, medical compositions comprising same, and a microorganism capable of producing same.

2. Prior Art

The present inventors have already found a process in which a strain referred to as Streptomyces sp. KC-6643 that has been isolated from soil is cultured, from which there are isolated and collected antibiotics KA-6643-A and KA-6643-B each showing an excellent antibacterial activity against both gram-positive and gram-negative bacteria and a β-lactamase inhibiting activity. These substances as well as the process are disclosed in Japanese Laid-open Patent Application Nos. 55-139380 and No. 56-43284.

The present inventors have conducted a further investigation on culture broths of a strain of Streptomyces sp. KC-6643 and its mutants. They have found that novel antibiotics other than the substances KA-6643-A and KA-6643-B are produced in the culture broths and have succeeded in isolating such antibiotics from the culture broths.

SUMMARY OF THE INVENTION

According to one aspect of the present invention, there is provided an antibiotic comprising at least one substance represented by any one of the following formulae, or a salt or ester thereof:

(1) KA-6643-D
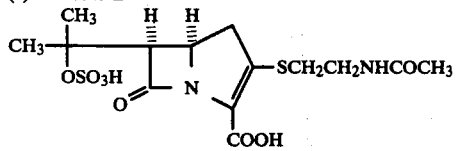

(2) KA-6643-F
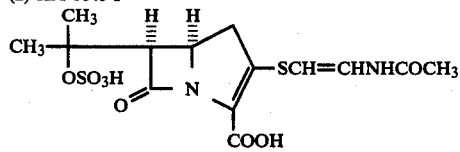

(3) KA-6643-G
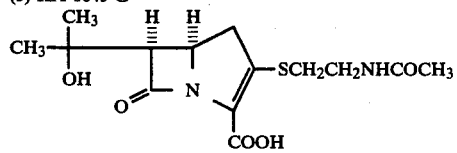

(4) KA-6643-X
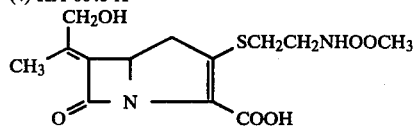

According to another aspect of the invention, there is provided a process for producing a KA-6643-series antibiotic represented by at least one of the following formulae, or a salt or ester thereof:

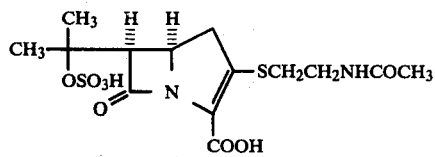 (1)

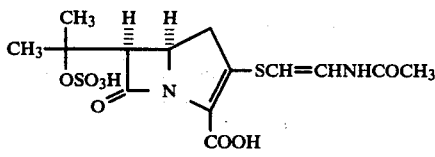 (2)

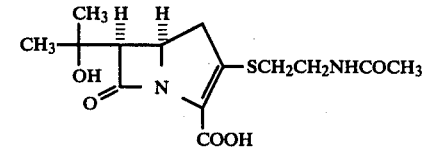 (3)

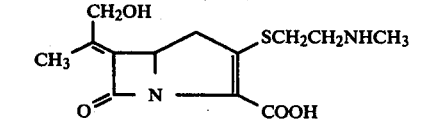 (4)

which process comprises culturing a strain belonging to the genus Streptomyces which can produce a KA-6643 substance, and isolating from the culture broth said KA-6643-series antibiotic, or a salt or ester thereof.

According to a further aspect of the invention, there is provided a medical composition comprising an effective amount of a KA-6643-series antibiotic represented by at least one of the following formulae, or a salt or ester thereof:

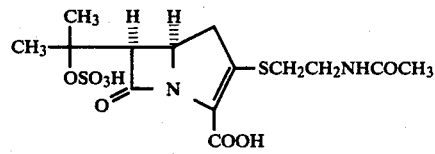 (1)

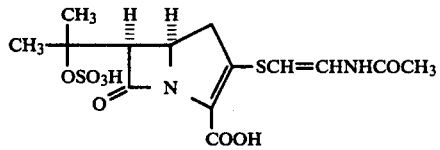 (2)

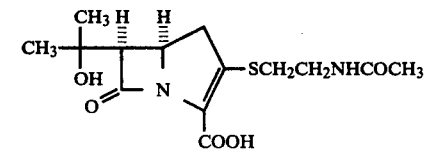 (3)

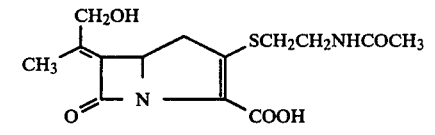 (4)

According to a still further aspect of the invention, there is provided a novel strain (FERM BP-58) belonging to the genus Streptomyces and designated as Streptomyces sp. KC-6643 M-162-175.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENT

Figure 1:
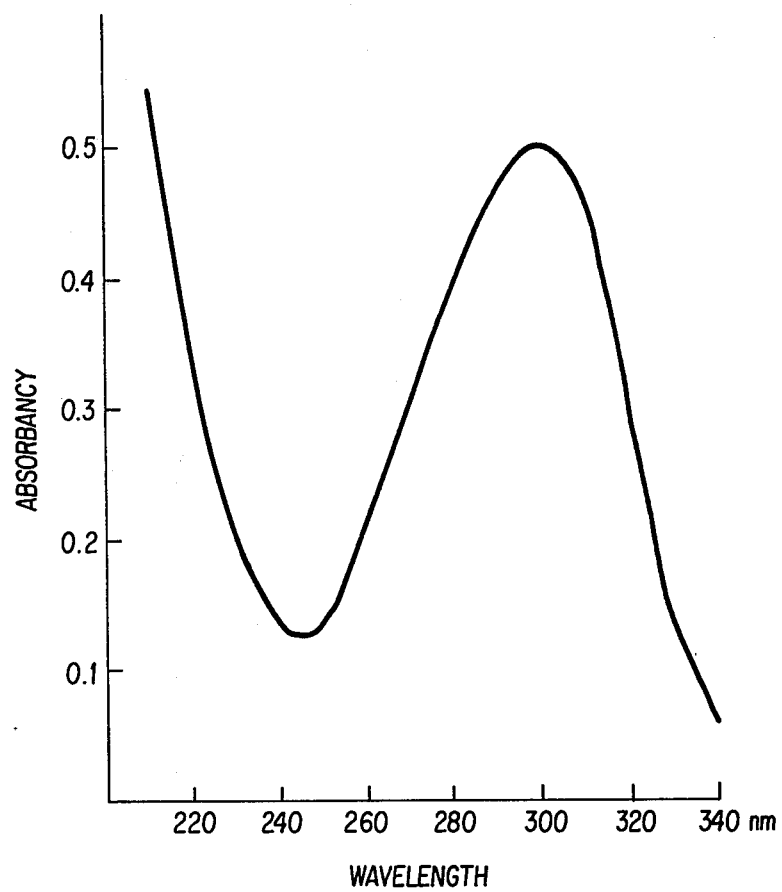
FIG. 1 is an ultraviolet absorption spectrum of a sodium salt of a substance KA-6643-D.

As is apparent from the physico-chemical and biological properties which will be described hereinafter, four antibiotics and salts and esters thereof according to the present invention are novel substances different from any known substances and are designated as KA-6643-D, KA-6643-F, KA-6643-G and KA-6643-X, respectively.

A suitable strain to be used in the invention, i.e. Streptomyces sp. KC-6643, was isolated from a soil sample collection in Sapporo-shi, Hokkaido, Japan and had the following morphological, cultural and physiological properties. It should be noted that the properties on various media are observed when cultured at 27° C. for 21 days by the usual method and that the color is expressed in accordance with the classification of the Color Harmoney Manual (Container Corporation of America), unless otherwise indicated.

(I) Morphological Properties

The present strain allows for the formation of an aerial mycelium on various media which is simply branched. The sporophore is produced on the aerial mycelium whereby straight spore chains are formed. Each of the spore chains is oval to cylindrical, 0.4–0.5μ×0.9–1.0μ in size, with a smooth surface, and consists of 20 or more spores. The spore chains are often entangled together to form a knot-like structure, and the fragmentation of the substrate mycelium is observed in some media.

(II) Culture Characteristics on Various Media (1) Sucrose-nitrate agar
 Growth: Good, flatly spreading, colorless - buff (2fb)
 Aerial mycelium: Moderate, powdery, white (a)
 Soluble pigment: None
(2) Glucose-asparagine agar
 Growth: Moderate, flat and buttery, cream (1½ ca) - pastel yellow (2hb)
 Aerial mycelium: None
 Soluble pigment: None
(3) Glycerol-asparagine agar
 Growth: Good, raised and convexed, rugose, buff (2fg) - bamboo (2gc)
 Aerial mycelium: Good, powdery, pearl (3ba)
 Soluble pigment: None
(4) Inorganic salt-starch agar
 Growth: Good, rugose, buttery, bamboo (2gc) - honey gold (2ic)
 Aerial mycelium: Good, powdery, white (a) - pearl (3ba)
 Soluble pigment: None
(5) Tyrosine agar
 Growth: Good, slightly raised, rugose, gelatinous, cinnamon (3le)
 Aerial mycelium: Good, powdery, pearl (3ba)
 Soluble pigment: None
(6) Nutrient agar
 Growth: Moderate, slightly raised, rugose, gelatinous, colorless - light yellow (1½ ea)
 Aerial mycelium: None
 Soluble pigment: None
(7) Yeast extract-malt extract agar
 Growth: Abundant, rugose, buttery-gelatinous, mustard (2le)
 Aerial mycelium: Good, powdery, white (a) - pearl, (3ba)
 Soluble pigment: None
(8) Oatmeal agar
 Growth: Moderate, flatly spreading, cream (1½ ca) - butter yellow (1½ ga)
 Aerial mycelium: Moderate, powdery, white (a)
 Soluble pigment: None
(9) Peptone-yeast extract-iron agar
 Growth: Good, slightly warty, rugose, buttery, light yellow (1½ ea)
 Aerial mycelium: None
 Soluble pigment None

(III) Physiological Properties

| | |
|---|---|
| (1) Growth temperature range: | 3–35° C. |
| (2) Optimum growth temperature range: | 27–33° C. |
| (3) Liquefaction of gelatin: | Positive |
| (4) Hydrolysis of starch: | Positive |
| (5) Coagulation of skim milk: | Negative |
| (6) Peptonization of skim milk: | Positive |
| (7) Formation of melanoid pigment: | Negative |

(IV) Utilization of Carbon Sources

The utilization of carbon sources was examined by the method of Pridham and Gottlieb with the following results.

Utilized carbon sources: L-arabinose, D-xylose, D-glucose, D-furactose, inositol and L-rhamnose Non-utilized carbon sources: Sucrose, raffinose and D-mannitol (V) The present strain contains LL-diaminopimelic acid in cell walls.

In view of the foregoing properties, the strain KC-6643 is believed to belong to the genus Streptomyces but shows characteristic properties such as the fragmentation of the substrate mycelium, the knot-like structure formation of the spore chains, and the like which are slightly different from those of the typical mycelia of the genus Streptomyces. However, it is widely known that the strains classified as belonging to the genus Streptomyces often assume such specific structures as for example of the fragmentation of hypha in the medium and the knot-like structure formation in the spore chains, and hence, it would be reasonable to consider that the strain belongs to the genus Streptomyces.

When strains of the nature in which the spore chain is straight, the spore surface is smooth, the aerial mycelium is white, the colony back side does not show any characteristic tinge, and the strains do not produce any soluble pigment or melanoid pigment, are searched for from known strains indicated in "Bergy's Manual of Determinative Bacteriology", 8th Edition, ISP Description of Shirling and Gottlieb, and "The Actinomyces" by S. A. Waksman, Vol. 2, there may be mentioned seven possible strains including *Streptomyces albovinaceous* (ISP 5136), *Streptomyces aureocircuratus* (ISP 5386), *Streptomyces baarnensis* (ISP 5232), *Streptomyces chrysomallus* (ISP 5128), *Streptomyces candidus* (ISP 5141), *Streptomyces gougeroti* (ISP 5324) and *Streptomyces griseoloalbus* (ISP 5468).

The *Streptomyces albovinaceous* (ISP 5136) is different from the strain KC-6643 in that the former is poor in growth on a sucrose-nitrate agar medium and in growth at 5° C. on various media, and in liquefaction of gelation and further in utilization of carbon sources (i.e. it utilizes D-mannitol not inositol). The *Streptomyces aureocirculatus* (ISP 5386) differs from the strain KC-6643 in that the former is poor in forming its aerial mycelium and grows at 37° C. but poorly at 5° C. and that it is weak in hydrolysis of starch and shows different degrees of ability to utilize carbon sources (i.e. it utilizes D-mannitol not L-rhamnose). The *Streptomyces candidus* (ISP 5141) differs from the strain KC-6643 in that the former is poor in growth on a sucrose nitrate agar medium and hardly grows at 5° C. and also in utilization of carbon sources (i.e. it utilizes D-mannitol not L-rhamnose). The *Streptomyces gougeroti* (ISP 5324) differs from the strain KC-6643 in that the former is poor in growth on a sucrose nitrate agar medium and in formation of its aerial mycelium, and also in liquefaction of gelatin, peptonization of skim milk and utilization of carbon sources (i.e. it utilizes L-mannitol not inositol nor L-rhamnose). The *Streptomyces griseoloalbus* (ISP 5468) differs from the strain KC-6643 in that the former grows at 37° C. but goes not grow at 5° C. and is weak in liquefaction of gelatin, utilization of carbon sources (i.e. it utilizes D-mannitol) and formation of a slight yellow tinge of its aerial mycelium. The *Streptomyces baarnensis* (ISP 5232) is relatively similar in culture nature to the strain KC-6643 but is different in that the former is poor in growth at 5° C. and produces a brown soluble pigment in a gelatin medium, and is also poor in utilization of carbon sources (i.e. it utilizes D-mannitol not inositol). The *Streptomyces chrysomallus* (ISP 5128) is relatively similar in culture nature to the strain KC-6643 but does not grow at 5° C. or in a skim milk medium. Further, it differs from the strain KC-6643 in formation of a yellow soluble pigment in several media and utilization of carbon sources (i.e. it utilizes D-mannitol not inositol).

As a strain capable of producing a product similar to a metabolite of the strain KC-6643, there are known 32 strains belonging to 11 species including *Streptomyces cattleya, Streptomyces flavogriseus, Streptomyces olivaceus, Streptomyces flavovires, Streptomyces flavus, Streptomyces fulvoviridis, Streptomyces argenteolus, Streptomyces sioyaensis, Streptomyces lipmanii, Streptomyces cremeus,* and *Streptomyces gedanensis.* However, none of these strains have such a nature that the aerial mycelium is white in color and that inositol not D-mannitol is utilized.

From the above results, the present inventors have concluded that the strain KC-6643 is a novel strain belonging to the genus Streptomyces and have designated it as Streptomyces sp. KC-6643. This strain was deposited at the Fermentation Research Institute of the Agency of Industrial Science & Technology of Japan and has been given Acceptance No. FERM-P 4467. The strain was also deposited at the American Type Culture Collection of the United States and has been given ATCC Acceptance No. ATCC 31493.

Preferable mutants of the strain KC-6643 used in the present invention include Streptomyces KC-6643 M-162-175. This strain is one which is obtained by treating the strain Streptomyces sp. KC-6643 by a combination of various types of artificial and spontaneous mutation and by further treating the resulting strain KC-6643 M-120-165 with N-methyl-N'-nitro-N-nitrosoguanidine as will be described hereinafter. The afore-mentioned substraces KA-6643-A and KA-6643-B are not recognized in the cultured broth of the present strain. The biological properties of this mutant are almost the same as those of the strain Streptomyces KC-6643, but the strains are different from each other in productivity. For instance, the strain KC-6643 M-162-175 is capable of producing substances KA-6643-D, KA-6643-F, KA-6643-G and KA-6643-X, while the substances KA-6643-G and KA-6643-X are not recognized in the cultured broth of the strain KC-6643. Accordingly, the present strain is believed to be a novel one and is designated as Streptomyces sp. KC-6643 M-162-175. This strain was deposited as the Fermentation Research Institute of the Agency of Industrial Science & Technology of Japan and has been given Acceptance No. 5890 (International Acceptance No. FERM BP-58).

The manner of mutation of from the strain KC-6643 M-120-165 into the strain KC-6643 and M-162-175 is described hereinafter. That is, to a suspension of the mycelia of the strain KC-6643 M-120-165 is added N-methyl-N'-nitro-N-nitrosoguanidine such that the final concentration is 200 γ/ml, followed by shaking at 30° C. for 1 hour. The reaction solution is then diluted and spread out on a yeast extract-malt extract agar medium for culture at 30° C. for 7 days. Thereafter, a grown colony is collected to obtain a strain KC-6643 M-162-175.

In the practice of the invention, there may be used not only the strains KC-6643 and KC-6643 M-162-175 themselves but also their spontaneous and artificial mutants.

The culture of these strains is feasible by any ordinary method of culturing actinomyces. As a carbon source for media, a variety of sources are usable. Preferably, starch, glycerine, maltose, dextrin, fructose, molasses and the like are used singly or in combination. Use can also be made of hydrocarbons, organic acids, plant oils and the like. Nitrogen sources include soybean flour, yeast extracts, dry yeast, peptone, meat extracts, corn steep liquors, Casamino acid, distiller's soluble, ammonium chloride, ammonium sulfate, urea, sodium nitrate and the like. These sources may be used singly or in combination. If necessary, inorganic salts such as sodium chloride, potassium phosphate, sodium phosphate, magnesium sulfate, potassium chloride, calcium carbonate, calcium hydroxide, cobaltous chloride, zinc sulfate, iron chloride, iron sulfate and the like, and traces of heavy metals may be added. Further, organic and inorganic substances which facilitate the production of the KA-6643-type substances such as methionine, cysteine, cystine and the like may be appropriately added. When an aerated culture method is employed, an anti-foamer such as fatty oil, silicone oil or paraffin is suitably added.

Although a culture of the strain in a solid medium is possible, a liquid culture, particularly a submerged culture, is preferably used as in the case where ordinary antibiotics are produced. Such culture is conducted under aerobic conditions at temperatures ranging from 3° to 35° C., preferably 27° to 33° C.

The KA-6643-type substances according to the invention can be produced by either a shaking culture or a tank culture. When such culture is continued for 2 to 10 days, an active substance is accumulated in the culture broth. The culture is terminated at the time the amount of the product in the culture broth reaches the maximum value, and an intended antibiotic is isolated from the culture broth and purified.

In order to isolate the KA-6643-series substances from the thus obtained culture broth and to purify the isolated substances, various known methods may be used as are usually employed for such purposes.

Isolation of KA-6643-D and KA-6643-F:

For instance, the culture broth may first be centrifugated or filtered to remove the mycelia therefrom, and the filtrate subjected to any arbitrary combination of the following treatments. The filtrate may be passed through a basic anion exchange resin to allow an active fraction to be adsorbed on the resin, and the active fraction may be obtained by eluting with a salt solution or an aqueous methanolic solution of the salt. Examples of such ion exchange resin include strongly basic anion exchange resins such as Dowex 1×2 (Dow Chemical Co.), Diaion PA-318, 316, 306S, 308 and 312 (Mitsubishi Kasei Kogyo Co.), and Amberlite IRA-400, 401 and 410 (Rohm & Haas Co.) and the like, moderately basic anion exchange resins such as Amberlite IRA-68, and weakly basic anion exchange resins such as DEAE-Sephadex (Pharmacia Fine Chemicals), DEAE-cellulose and the like. Alternatively, the culture filtrate may be subjected to adsorption with an adsorbent such as active carbon or an active fraction obtained by elution with aqueous methanol, aqueous acetone or like solvent.

Still alternatively, the culture broth may be extracted with an organic solvent such for example as chloroform, dichloromethane or the like, which contains a quaternary ammonium salt such as trioctylmethylammonium chloride, tricaprylmethylammonium chloride or the like, and subjected to back extraction with an aqueous solution of sodium iodide, sodium chloride or the like.

Thereafter, the active fraction is passed through a column packed with a strongly basic ion exchange resin such for example as Dowex 1×2 for adsorption thereon, after which the fraction is stepwise eluted while gradually changing a salt concentration in a phosphate buffer solution. In this elution operation, the substance KA-6643-A is eluted at an initial stage, then a mixture of the substances KA-6643-B and KA-6643-D is eluted, and finally the substance KA-6643-F is eluted. Alternatively, the active fraction may be passed through a column packed with a moderately polar or non-polar, hydrophobic cross-linked polymer such for example as Amberlite XAD-2 or Diaion HP-20 to separate the substances KA-6643-A, KA-6643-B, KA-6643-D and KA-6643-F due to the their adsorptivity differences.

Still alternatively, the active fraction may be subjected to reversed phase chromatography using a column packed with a moderately polar or non-polar, hydrophobic cross-linked polymer such for example as Bondapak $C_{18}$ (Waters Associates, Inc.), thereby obtaining highly pure substances of KA-6643-D and KA-6643-F.

Isolation of KA-6643-D, KA-6643-F, KA-6643-G and KA-6643-X:

For instance, the filtrate obtained by the method mentioned above may be extracted with an organic solvent such for example as chloroform, dichloromethane or the like, which contains a quaternary ammonium salt such for example as trioctyl-methylammonium chloride, tricapryl-methylammonium chloride or the like. Thereafter, the organic solvent layer is purified by the method of separation of KA-6643-D and KA-6643-F as described above. On the other hand, the aqueous layer which contains KA-6643-G and KA-6643-X may be passed through a basic anion exchange resin to allow an active fraction to be adsorbed on the resin, and the active fraction is eluted with a salt solution or an aqueous methanolic solution of the salt. Examples of such ion exchange resin include strongly basic anion exchange resins such as Dowex 1×2, Diaion PA-138, 136, 306S, 308 and 312, Amberlite IRA-400, 401 and 410, and the like, moderately basic anion exchange resins such as Amberlite IRA-68, and weakly basic anion exchange resins such as DEAE-Sephadex, DEAE-cellulose and the like. Alternatively, the culture filtrate may be subjected to adsorption with an adsorbent such as active carbon and an active fractions obtained by elution with aqueous methanol, aqueous acetone or the like.

The thus eluted active fraction is further passed through a column packed with a strongly basic ion exchange resin such for example as Dowex 1×2 to adsorb the intended substances thereon after which they are eluted stepwise while gradually changing a salt concentration in a phosphate buffer solution, or passed through a column packed with a moderately polar or non-polar, hydrophobic cross-linked polymer such for example as Amberlite XAD-2 or Diaion HP-20, thereby isolating and collecting a mixture of KA-6643-G and KA-6643-X.

Then, the thus obtained mixture of KA-6643-G and KA-6643-X is further subjected to gel filtration using a gel such as Biogel P-2 (BIO RAD Lab.) or Sephadex G-10 (Pharmacia Fine Chemicals), or subjected to reverse phase chromatography using a column packed with Bondapak $C_{18}$ (Waters Associates, Inc.), thereby separating the mixture into the substance KA-6643-X and the substance KA-6643-G.

The thus obtained substances KA-6643-D, KA-6643-F, KA-6643-G and KA-6643-X may be converted by any usual methods to alkali metal salts; alkaline earth metal salts; primary, secondary or tertiary amine salts; or quaternary ammonium salts; or esters thereof.

The antibiotics according to the invention have the following physico-chemical and biological properties, and exhibit antibacterial activities against gram-negative bacteria and also potential β-lactamase inhibitory activities.

(I) Physico-chemical Properties of Sodium Salt of Substance KA-6643-D (1) Appearance: Colorless powder (2) Molecular formula: $C_{14}H_{18}N_2O_8S_2 \cdot Na_2$ (3) Ultraviolet absorption spectrum: The spectrum of the substance taken in an aqueous solution is substantially the same as shown in FIG. 1 with maximum absorption at 300 nm.

Figure 2:
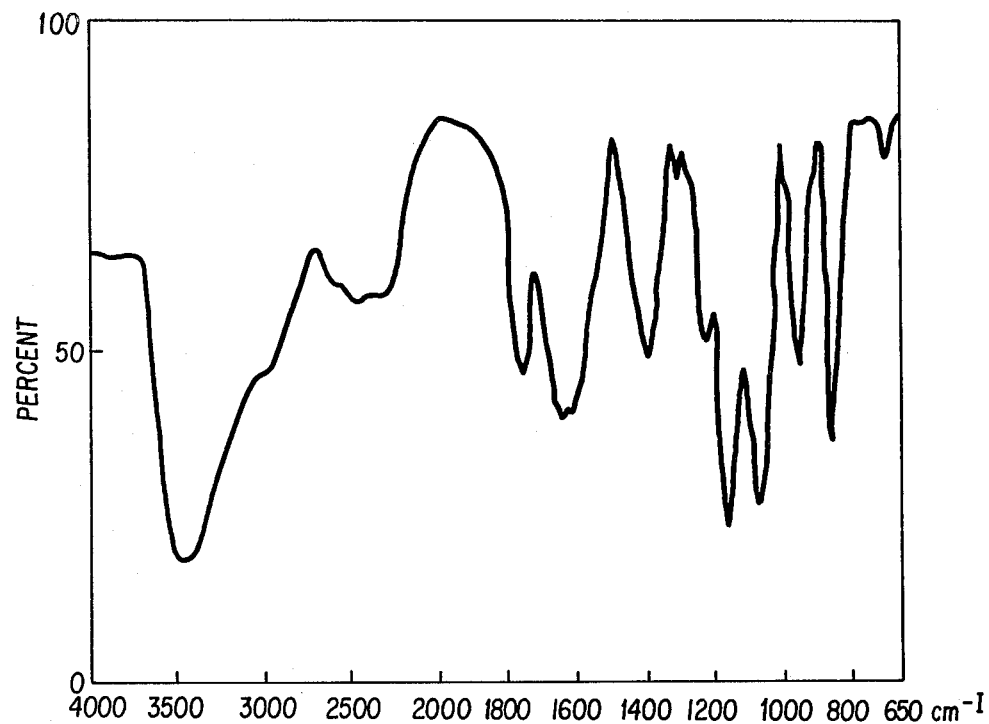
FIG. 2 is an infrared absorption spectrum of the just-mentioned salt.

(4) Infrared absorption spectrum: The spectrum of the substance taken in a KBr tablet is substantially the same as shown in FIG. 2.

(5) Solubility in solvents: Readily soluble in water but substantially insoluble in organic solvents such as acetone, chloroform, ethyl acetate and petroleum ether (6) Color reaction: Positive in Rydon-Smith reaction and negative in ninhydrin reaction and Sakaguchi's reaction (7) Thin layer chromatography:

| Plate: | Cellulose $F_{254}$ (Merck & Co., Inc.) |
|---|---|
| Solvent: | N—Butanol-i-propanol-water (7:7:6) |
| Rf value: | 0.40 |

(8) High performance liquid chromatography:

| Column: | Bondapak $C_{18}$/Porasil B, 2 × 600 mm |
|---|---|
| Solvent: | 0.2M Phosphate buffer solution (pH 7.8) |
| Flow rate: | 1.0 ml/min |
| Retention time: | 35 minutes |

From the above various properties, the substance KA-6643-D has been adjudged to have the following structural formula:

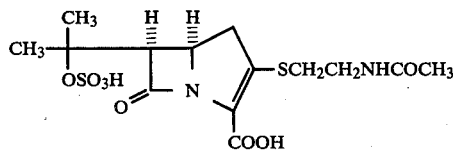

(II) Biological Properties of Sodium Salt of Substance KA-6643-D (1) Antibacterial activity-improving action against β-lactam-resistant bacteria (Disc method):

In Penassay agar (Kyoei Pharm. Co., Ltd.) in which 200 mcg/ml of aminobenzyl penicillin (AB-PC) was inoculated germs of *Escherichia coli* ML-1410R EC-1 which β-lactamase-producing organisms, and 10 ml of the inoculated medium were poured on a Petri disch of 9 cm in diameter and solidified to give a test medium.

On this agar medium were placed pulp discs of 8 mm in diameter into which were respectively introduced 30 μg of aqueous solutions of the substance KA-6643-D with a concentration of 10 mcg/ml followed by culturing at 37° C. for 18 hours and measuring the diameter of an inhibition zone around each disc. For purposes of control, the above experiment was repeated using the same type of medium in which no AB-PC was added. The results are shown in Table 1.

TABLE 1

| Tested organism | Diameter of inhibitory zone (mm) Present compound (10 mcg/ml) |
|---|---|
| *Escherichia coli* ML-1410R EC-1 | 0 |

TABLE 1-continued

| Tested organism | Diameter of inhibitory zone (mm) Present compound (10 mcg/ml) |
|---|---|
| *Escherichia coli* ML-1410R EC-1 and AB-PC (200 mcg/ml) | 22.0 |

Figure 3:
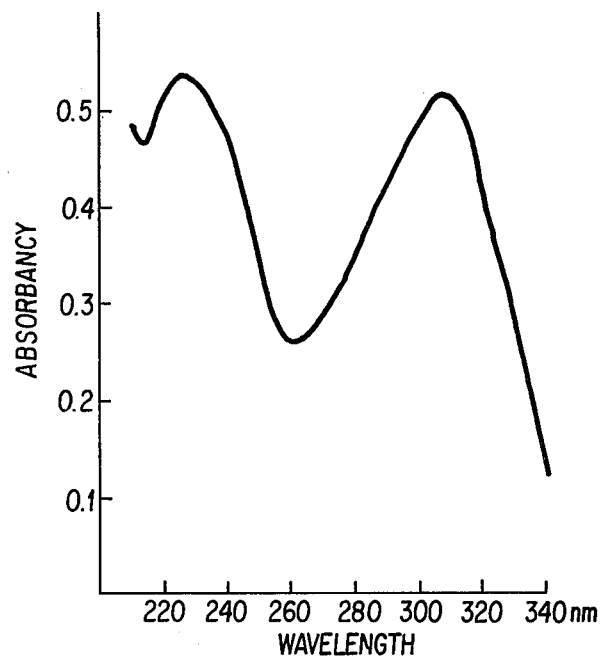
FIG. 3 is an ultraviolet absorption spectrum of a sodium salt of a substance KA-6643-F.

(III) Physico-chemical Properties of Sodium Salt of Substance KA-6643-F (1) Appearance: Colorless powder (2) molecular formula: $C_{14}H_{16}N_2O_8S_2$ (3) Ultraviolet absorption spectrum: The spectrum of the substance taken in an aqueous solution is substantially the same as shown in FIG. 3 with maximum absorption at 227 nm and 308 nm.

Figure 4:
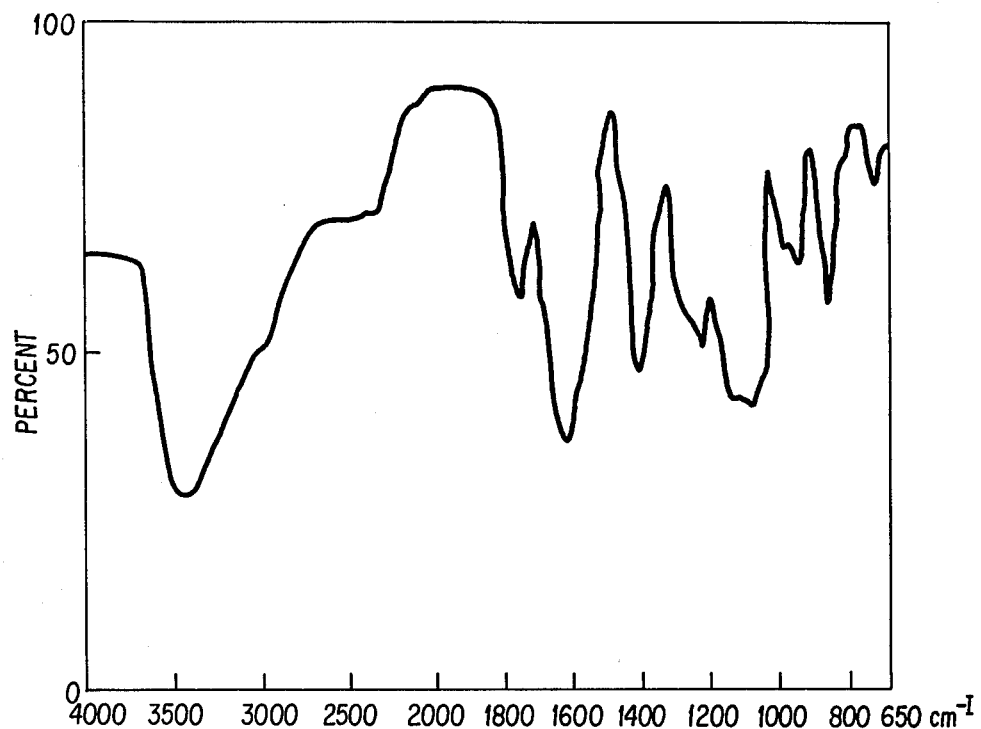
FIG. 4 is an infrared absorption spectrum of the just-mentioned salt.

(4) Infrared absorption spectrum: The spectrum of the substance taken in a KBr tablet is substantially the same as shown in FIG. 4.

(5) Solubility in solvent: Readily soluble in water but substantially insoluble in organic solvents such as acetone, chloroform, ethyl acetate and petroleum ether (6) Color reaction: Positive in Rydon-Smith reaction and negative in ninhydrin reaction and Sakaguchi's reaction (7) Thin layer chromatography:

| Plate: | Cellulose $F_{254}$ (Merck & Co., Inc.) |
|---|---|
| Solvent: | n-Butanol-i-propanol-water (7:7:6) |
| Rf value: | 0.45 |

(8) High performance liquid chromatography:

| Column: | Bondapak $C_{18}$/Porasil B, 2 × 600 mm |
|---|---|
| Solvent: | 0.2M Phosphate buffer solution (pH 7.8) |
| Flow rate: | 1.0 ml/min |
| Retention time: | 80 minutes |

From the above characteristic properties, the substance KA-6643-F has been adjudged to have the following structural formula:

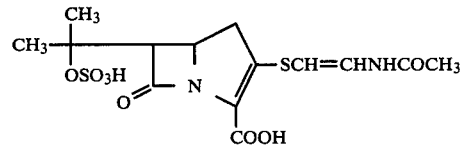

(IV) Biological Properties of Sodium Salt of Substance KA-6643-F

The synergistic effect of the present substance and Ampicillin (aminobenzyl penicillin, AB-PC) on *Escherichia coli* which is resistant to Ampicillin was investigated by the disc method similarly to item (II) above with the results shown in Table 2.

TABLE 2

| Tested organism | Inhibitory zone (mm) Present substance (15 mcg/ml) |
|---|---|
| *Escherichia coli* ML-1410 | 0 |

TABLE 2-continued

| Tested organism | Inhibitory zone (mm) Present substance (15 mcg/ml) |
| --- | --- |
| R EC-1 *Escherichia coli* ML-1410 | 24.0 |
| R EC-1 and AB-PC (200 mcg/ml) | |

Figure 5:
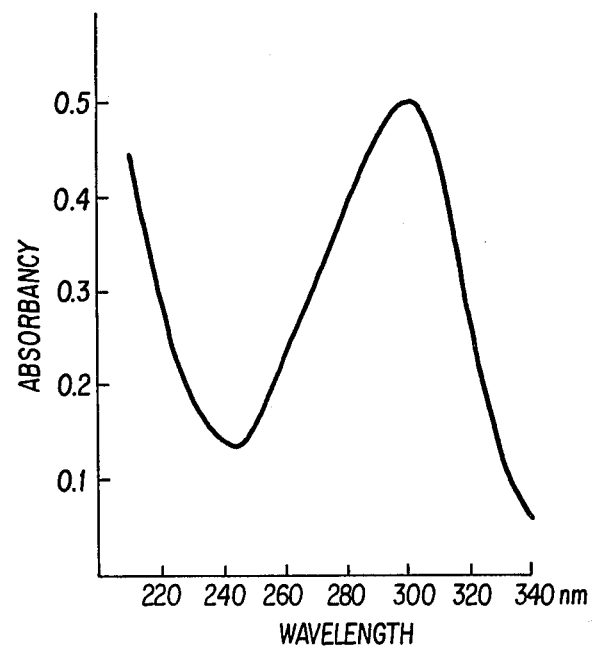
FIG. 5 is an ultraviolet absorption spectrum of a sodium salt of a substance KA-6643-G.
Figure 6:
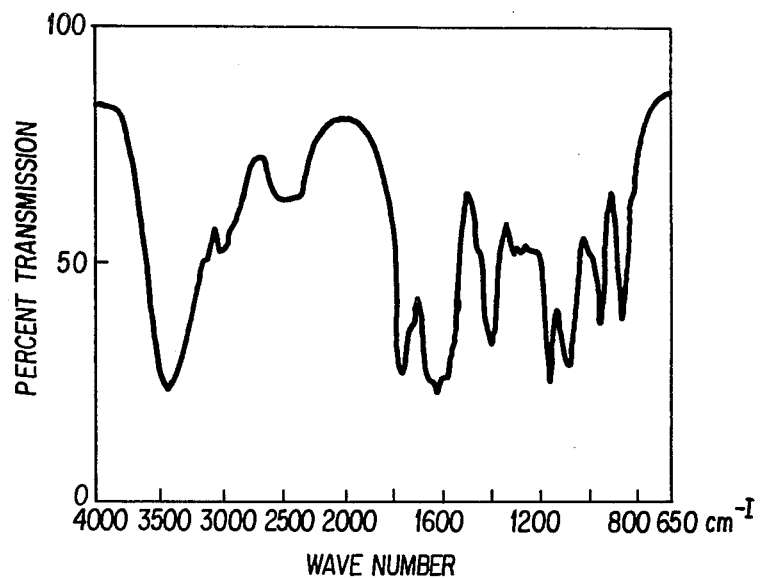
FIG. 6 is an infrared absorption spectrum of the just-mentioned salt.
Figure 7:
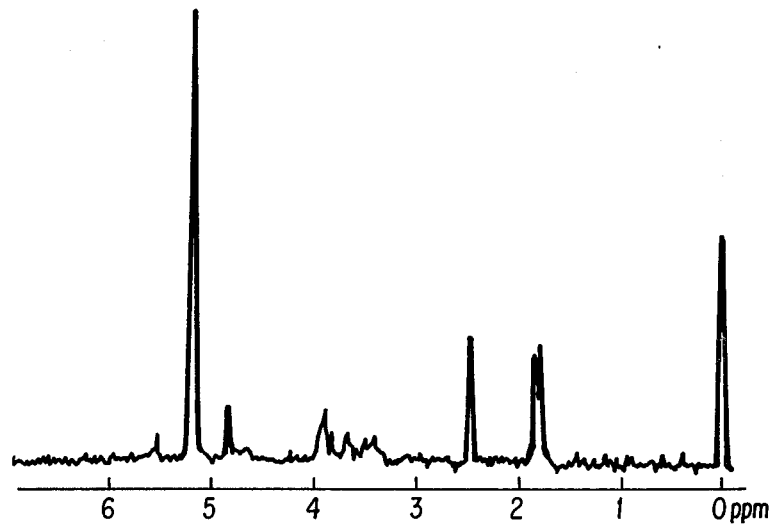
FIG. 7 is a $^1$H-NMR spectrum of the just-mentioned salt.

(V) Physico-chemical Properties of Sodium Salt of Substance KA-6643-G (1) Appearance: White powder
(2) Molecular weight: Based on the mass spectrum value of the methyl ester Found: 342.1224 Calculated: 342.1246 (for $C_{15}H_{22}N_2O_5S$)
(3) Molecular formula: $C_{14}H_{19}N_2O_5S \cdot Na$
(4) Ultraviolet absorption spectrum: The spectrum taken in an aqueous solution is substantially the same as shown in FIG. 5 with maximum absorption at 302 nm.
(5) Infrared absorption spectrum: The spectrum of the substance taken in a KBr tablet is substantially the same as shown in FIG. 6.
Main peak
$\nu_{max}^{KBr}$ 1760 cm$^{-1}$ ($\beta$-lactam)
(6) $^1$H-NMR spectrum: On measurement in D$_2$O, the spectrum of the substance is substantially the same as shown in FIG. 7.
Main peaks
$\delta$ D$_2$O ppm: 1.78 (3H, s, C-C$_3$), 1.83 (3H, s, C-CH$_3$), 2.25 (3H, s, COCH$_3$).
(7) Thin layer chromatography:

| Plate: | Cellulose F$_{254}$ (Merck & Co., Inc.) |
| --- | --- |
| Solvent | Rf value |
| (a) Butanol-isopropanol-water (7:7:6): | 0.68 |
| (b) Ethanol-water (7:3): | 0.88 |

(8) High performance liquid chromatography:

| Column: | Radial Pak A (Waters Associates, Inc.) 0.8 × 10 cm | |
| --- | --- | --- |
| Solvent | Flow rate | Retention time |
| (a) Methanol-0.1M potassium phosphate (12:88, pH 4.6) | 2.0 ml/min | 18.9 minutes |
| (b) Methanol-0.1M phosphate buffer solution (12:88, pH 8.6) | 1.0 ml/min | 25.2 minutes |

(9) Solubility: Soluble in water and methanol but substantially insoluble in acetone, ethyl acetate and chloroform
(10) Color reaction: Positive in Ehrlich's reaction and negative in ninhydrin reaction From the above-indicated various properties, the substance KA-6643-G has been assumed to have the following structural formula:

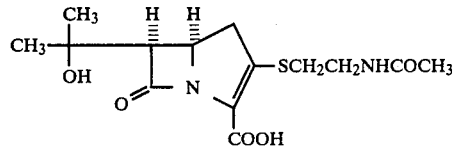

(VI) Biological Properties of Sodium Salt of Substance KA-6643-G (1) Antibacterial activity-improving action against $\beta$-lactam-resistant bacteria:

The synergistic effect of the present substance and Ampicillin (AB-PC) on the Ampicillin-resistant *Escherichia coli* was investigated by the disc method similarly to the case of item (II) above, except that AB-PC was used in an amount of 500 mcg/ml. The results are as shown in Table 3.

TABLE 3

| Concentration of present substance (mcg/ml) | Inhibitory zone (mm) |
| --- | --- |
| 0 | — |
| 250 | 20.5 |
| 500 | 22.5 |
| 1,000 | 24.5 |

(2) Stability: The rate of decomposition with dehydropeptidase which had been extracted from the kidney of a pig and purified was 1 for the substance KA-6643-A and $2.5 \times 10^{-3}$ for the substance KA-6643-G.

Figure 9:
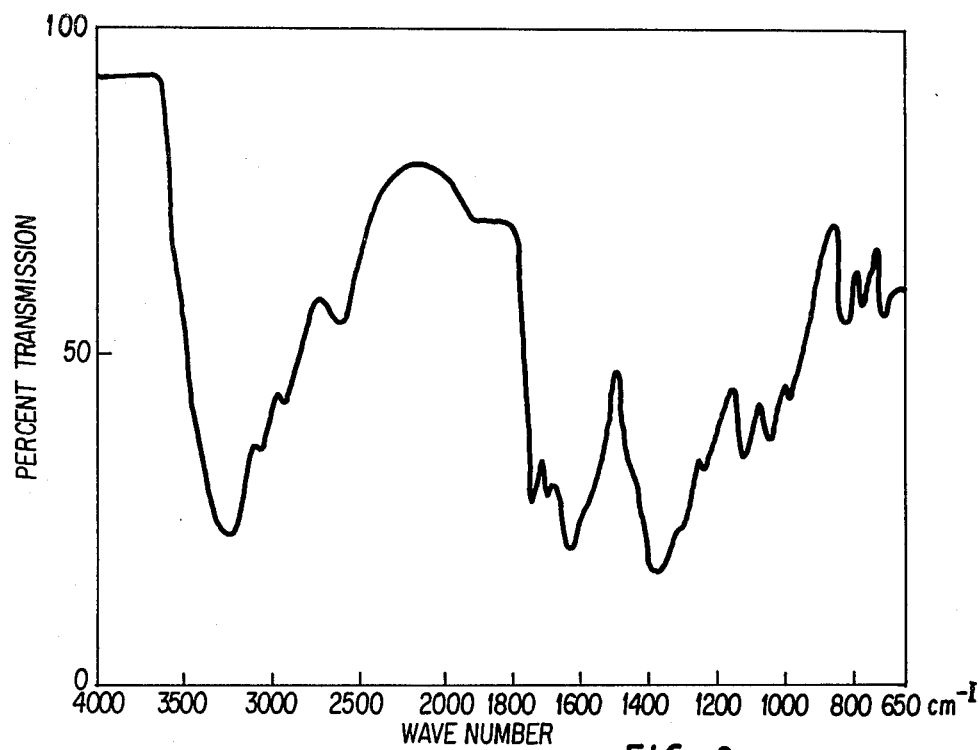
FIG. 9 is an infrared absorption spectrum of the just-mentioned salt.
Figure 8:
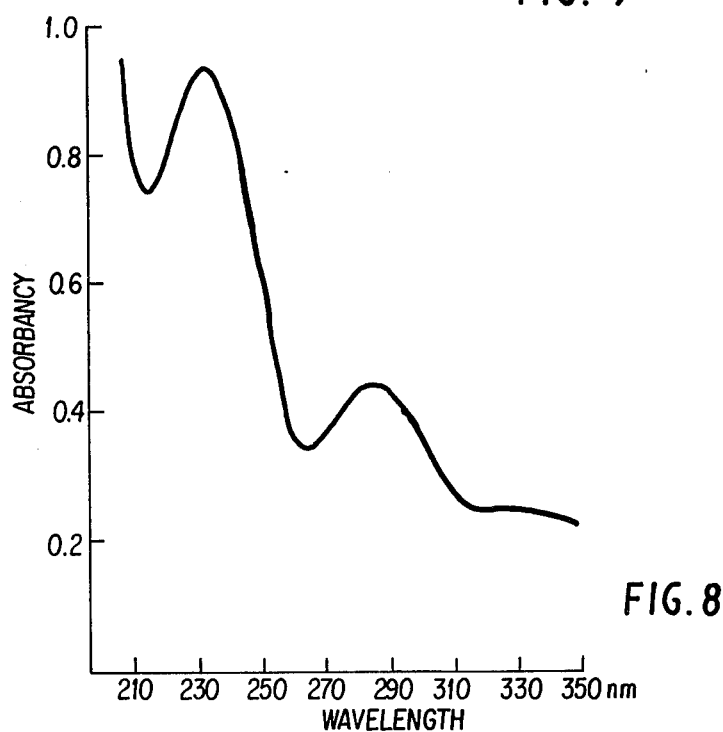
FIG. 8 is an ultraviolet absorption spectrum of a sodium salt of a substance KA-6643-X.

(VII) Physico-chemical Properties of Sodium Salt of Substance KA-6643-X (1) Appearance: Colorless powder
(2) Molecular weight: Mass spectrum of the methyl ester Found: 340.1068 Calculated: 340.1090 (for $C_{15}H_{20}N_2O_5S$)
(3) Molecular formula: $C_{14}H_{17}N_2O_5S \cdot Na$
(4) Ultraviolet absorption spectrum: The spectrum of the substance taken in an aqueous solution is substantially the same as shown in FIG. 8 with maximum absorption at 235 nm and 285 nm.
$\nu_{max}^{H_2O}$ 235 nm, 285 nm
(5) Infrared absorption spectrum: The spectrum of the substance taken in a KBr tablet is substantially the same as shown in FIG. 9.
Main peak
$\nu_{max}^{KBr}$ 1740 cm$^{-1}$ ($\beta$-lactam)
(6) $^1$H-NMR spectrum: On measurement of the methyl ester at 200 MHz using TMS as an internal standard, the main peaks are as follows:
$\delta$ CDCl$_3$ ppm: 1.98 (s, 3H), 2.02 (s, 3H), 3.87 (s, 3H).
(7) Thin layer chromatography:

| | Rf value |
| --- | --- |
| Cellulose plate (Merck & Co., Inc.) Solvent | |
| Butanol-isopropanol-water (7:7:6): | 0.67 |
| Isopropanol-water (7:3): | 0.84 |

(8) High performance liquid chromatography:

| Column: | Radial Pak A (Waters Associates, Inc.) 0.8 × 10 cm |
| --- | --- |
| Solvent: | 1.2% methanol/0.05M phosphate buffer solution (pH 6.8) |
| Flow rate: | 1.0 ml/min |
| Retention time: | 14.5 minutes |

(9) Solubility: Soluble in water and methanol but substantially insoluble in acetone, ethyl acetate, chloroform and ether

(10) Color reaction: Positive in Ehrlich reaction and negative in ninhydrin reaction From the above-indicated various properties, the substance KA-6643-X has been adjudged to have the following structural formula:

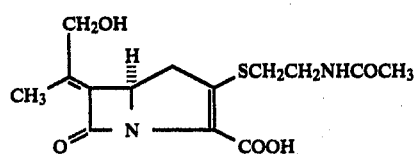

(VIII) Biological Properties of Sodium Salt of Substance KA-6643-X (1) Antibacterial activity-improving action against β-lactam-resistant bacteria:

The synergistic effect of the present substance and Ampicillin (AB-PC) on the Ampicillin-resistant *Escherichia coli* was investigated by the disc method similarly to the case of item (II) above. The results are as shown in Table 4.

TABLE 4

| Concentration of present substance (mcg/ml) | Diameter of inhibitory zone (mm) | |
|---|---|---|
| | No AB-PC added | AB-PC added |
| 50 | 21.0 | 23.0 |
| 25 | 19.0 | 21.5 |

(IX) Antibacterial Spectrum

The antibacterial spectra of the substances according to the invention are shown in Table 5.

TABLE 5

| | Minimum inhibitory concentration (mcg/ml) | | | |
|---|---|---|---|---|
| Tested organism | KA-6643-D | KA-6643-F | KA-6643-G | KA-6643-X |
| *Staphylococcus aureus* 209P JC-1 | 25 | 12.5 | 6.25 | 1.56 |
| *Escherichia coli* NIHJ JC-2 | 3.1 | 12 | >25 | 0.05 |
| *Klebsiella pneumoniae* PCI-602 | 3.1 | 6.25 | >25 | 0.2 |
| *Proteus vulgaris* OX17 | 12.5 | 12.5 | >25 | 0.05 |
| *Proteus inconstants* | ND | ND | ND | 3.1 |
| *Enterobacter cloacae* IID 977 | 6.25 | 12 | >25 | 0.78 |
| *Pseudomonas aeruginosa* NCTC 10490 | 25 | >25 | >25 | 3.1 |

The present invention will now be described in further detail with reference to some non-limiting examples.

EXAMPLE 1

10 l of a liquid medium which had a composition of 3.6% starch, 2.2% of soybean flour, 0.1% of monobasic potassium phosphate, 0.62% of dibasic sodium phosphate dodecahydrate, 0.0005% of cobaltous chloride hexahydrate, 0.01% of ferrous sulfate heptahydrate, 0.05% of magnesium sulfate heptahydrate, and 1.5% of cotton seed oil and whose pH had been adjusted to 6.0 was provided, and aliquots of 30 ml of the medium were each charged into a 500 ml Erlenmeyer flask and sterilized. Mycelia of the strain KC-6643 were inoculated in the medium and cultured at 30° C. for 6 days at 220 r.p.m. After completion of the culture, the culture broth was centrifugated at 5,000 r.p.m. for 30 minutes to obtain 7 l of a supernatant liquid.

This supernatant liquid was extracted with 1.5 l of dichloromethane containing 1% of tricaprylmethylammonium chloride. The dichloromethane layer was back extracted with 500 ml of a 3% sodium iodide solution. To the aqueous layer was added 2.5 l of deionized water, followed by passing through a column (300 ml) packed with DEAE-Sephadex A-25 equilibrated with a phosphate buffer solution of pH 8 and by eluting by a concentration gradient method using deionized water and a 0.5M saline solution which had been, respectively, adjusted with an ammonia solution to pH 8.0, thereby separately collecting a fraction eluted at a salt concentration of 0.2M (hereinafter referred to as fraction D) and a fraction eluted at a salt concentration of 0.35M (hereinafter referred to as fraction F).

EXAMPLE 2

(1) To the fraction D obtained in Example 1 was added a solution of 2% of monobasic disodium phosphate dodecahydrate containing 20% of sodium chloride followed by passing through a column (150 ml) of Diaion HP-20 which had been previously washed with a 20% salt solution and by eluting with an ammonia solution of pH 8.0. The active fractions were collected and concentrated, and passing through a column (100 ml) of Sephadex G-10, followed by eluting with an ammonia solution of pH 8.0. The active fractions were concentrated and freeze dried to afford 93 mg of a crude powder of the substance KA-6643-D.

(2) 70 mg of this crude powder was dissolved in 1 ml of deionized water and eluted with a 0.2M phosphate buffer solution of pH 7.8 at a flow rate of 6 ml/min by high performance liquid chromatography using a column (2×120 cm) of Bondapak $C_{18}$/Porasil B. The eluate was cut into 6 ml fractions. Fraction Nos. 39–50 were collected and passed through a column (20 ml) of active carbon, washed with deionized water and eluted with an aqueous 50% acetone solution. The resulting active fractions were concentrated and freeze dried to afford 2.3 mg of a pure powder of a sodium salt of the substance KA-6643-D.

EXAMPLE 3

(1) The fraction F obtained in Example 1 was treated in the same manner as in (1) of Example 2 to afford 25 mg of a crude powder of the substance KA-6643-F.

(2) 25 mg of the crude powder was dissolved in 1 ml of deionized water and eluted with a methanol-0.05M phosphate buffer solution (2:98, pH 7.8) at a flow rate of 6 ml/min by high performance liquid chromatography using a column (0.8×120 cm) of Bondapak $C_{18}$/Porasil B, and 6 ml of each of the fractions was collected separately. Fraction Nos. 155–210 were collected together and concentrated, and passed through a column (180 ml) of Diaion HP-20, followed by eluting with an ammonia solution of pH 8.0. The resulting active fractions were concentrated and freeze dried to afford 1.2 mg of a pure powder of a sodium salt of the substance KA-6643-F.

EXAMPLE 4

A liquid medium which had a composition of 3.6% of corn starch, 2.2% of soybean flour, 1.5% cotton seed oil, 0.05% of magnesium sulfate heptahydrate, 0.1% of monobasic potassium phosphate, 0.62% of dibasic sodium phosphate dedecahydrate, 0.0005% of cobaltous chloride hexahydrate, 0.001% of ferrous sulfate heptahydrate and 0.02% of cysteine and whose pH had been adjusted to 6.0 was provided, and aliquots of 30 ml of the medium were charged into seven Erlenemeyer flasks and sterilized. Mycelia of Streptomyces sp. KC-6643 M-162-175 were inoculated in each medium and cultured on rotary shaking at 30° C. for 72 hours to give a first seed.

Seven jar fermentors each having a capacity of 20 l were charged with 10 l of a medium having such a composition as used above, except that soybean flour was used in an amount of 2.5% and the cotton seed oil was used in an amount of 2.0%. Thereafter, 30 ml of the first seed was transplanted into each fermentor, followed by culturing at 30° C. for 5 days by an aerated agitation system (agitation of 300 r.p.m., aeration of 20 l/min) and inner pressure of 0.5 kg/cm$^2$).

After completion of the culture, Dicalite was added as a filter aid to the culture broth, and the broth was filtered to give a filtrate of about 60 l.

This filtrate was extracted with 15 l of dichloromethane containing 1% of tricaprylmethylammonium chloride. The dichloromethane layer was back extracted with 5 l of a 3% sodium iodide aqueous solution. To the aqueous layer was added 25 l of deionized water, which was passed through a column (2 l) of DEAE-Sephadex A-25 equilibrated with a phosphate buffer solution of pH 8.0 and eluting by a concentration gradient method using deionized water and a 0.5M saline solution which had been, respectively, adjusted with an ammonia solution to pH 8.0, thereby separately collecting a fraction eluted at a salt concentration of 0.2M (hereinafter referred to as fraction D) and a fraction eluted at a salt concentration of 0.35M (hereinafter referred to as fraction F).

Then, these fractions were treated in the same manner as in Examples 2 and 3, respectively, to afford 20 mg of a pure powder, of a sodium salt of the substance KA-6643-D and 12 mg of a pure powder of a sodium salt of the substance KA-6643-F.

On the other hand, 15 l of the aqueous layer obtained at the time of extraction with dichloromethane was passed through a column (6×45 cm) packed with Diaion PA-306 which had been previously washed with a phosphate buffer solution of pH 8.0 and then washed with water, followed by eluting with a 0.05M phosphate buffer solution (pH 8.6) containing 20% of sodium chloride to collect an active fraction. 4 l of this fraction was passed through a column (4.5×50 cm) packed with Diaion HP-20 which had been washed with a 0.05M phosphate buffer solution (pH 8.0) containing 20% of sodium chloride, followed by washing with 1 l of a 0.05M phosphate buffer solution (pH 8.0) and eluting with a diluted ammonia solution of pH 8.0 to collect active fractions. The active fractions (1 l) were diluted with deionized water until the electrical conductivity of the resulting solution was 3 mΩ. Then, the solution was passed through a column (3.5×40 cm) of Dowex 1×2 equilibrated to pH 8.0 and eluted by a concentration gradient method between 1 l of a 0.05M phosphate buffer solution (pH 8.0) and 1 l of a 0.05M phosphate buffer solution (pH 8.0) having a sodium chloride concentration of 0.3M. 400 ml of an active fraction was collected, to which was added 400 ml of a 0.05M phosphate buffer solution (pH 8.0) containing 20% of sodium chloride, followed by passing for adsorption through a column (2×45 cm) packed with Diaion HP-20 which had been previously washed with a 0.05M phosphate buffer solution (pH 8.0) containing 20% of sodium chloride. Thereafter, the column was washed with 150 ml of a 0.05M phosphate buffer solution (pH 8.0) containing 10% of sodium chloride and then eluted with a diluted ammonia solution of pH 8.0 to collect an active fraction, followed by concentrating to about 2 ml under reduced pressure. The concentrate was passed through a column (2.2×90 cm) packed with Sephadex G-10 and then eluted with a diluted ammonia solution of pH 8.0. The active fractions were collected, concentrated and freeze dried to give 50.4 mg of a light yellow solid.

The thus obtained solid was dissolved in a 0.2M phosphate buffer solution of pH 7.8 and passed through a column (0.8×120 cm) of Bondapak C$_{18}$/Porasil B (Waters Associates, Inc.), followed by eluting with 1.5 l of the buffer solution of the just-mentioned type at a flow rate of 6 ml/min. The active fractions were collected, desalted with Diaion HP-20, concentrated and freeze dried to afford 4 mg of a pure powder of a sodium salt of the substance KA-6643-X.

After completion of the elution of the active fraction, the column was further eluted with 400 ml of deionized water to collect active fractions. The active fractions were concentrated and freeze dried to afford 2.5 mg of a pure powder of a sodium salt of the substance 6643-G.

What is claimed is:

1. A KA-6643-series antibiotic comprising at least one substance represented by any of the following formulae, or a pharmaceutically acceptable salt or ester thereof:

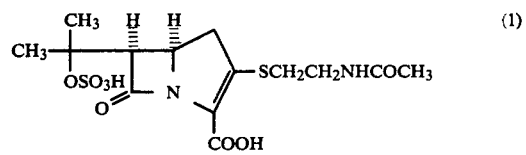

(1)

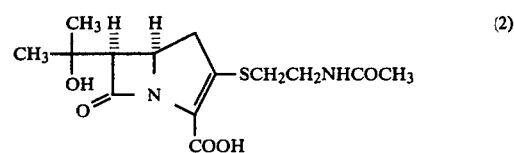

(2)

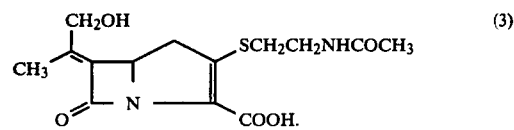

(3)

2. An antibiotic KA-6643-D represented by the following formula, or a pharmaceutically acceptable salt or ester thereof:

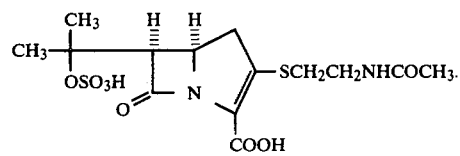

3. An antibiotic KA-6643-G represented by the following formula, or a pharmaceutically acceptable salt or ester thereof:
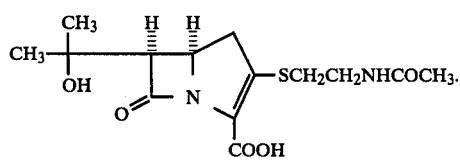
4. An antibiotic KA-6643-X represented by the following formula, or a pharmaceutically acceptable salt or ester thereof:
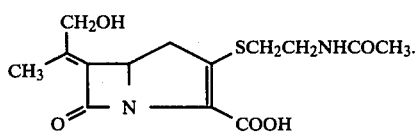
* * * * *